(12) United States Patent
Esser et al.

(10) Patent No.: US 6,444,855 B1
(45) Date of Patent: Sep. 3, 2002

(54) PROCESS FOR PREPARING CYCLIC ALCOHOLS AND KETONES

(75) Inventors: Peter Ernst Esser, Recklinghausen; Thomas Schiffer; Bernd Guenzel, both of Haltern; Georg Oenbrink, Duelmen, all of (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 09/492,193

(22) Filed: Jan. 27, 2000

(30) Foreign Application Priority Data

Jan. 27, 1999 (DE) .......................... 199 03 152

(51) Int. Cl.⁷ .......................... C07C 45/00; C07C 35/20
(52) U.S. Cl. ...................... 568/359; 568/821
(58) Field of Search ................ 568/360, 342, 568/836, 357, 359, 821, 837

(56) References Cited

U.S. PATENT DOCUMENTS

| | | | | |
|---|---|---|---|---|
| 3,419,615 A | * | 12/1968 | Inchalik et al. | 260/586 |
| 3,844,971 A | | 10/1974 | El-Ghatta et al. | |
| 4,341,907 A | | 7/1982 | Zelonka | |
| 5,221,773 A | * | 6/1993 | Nakamura et al. | 568/887 |
| 5,426,237 A | * | 6/1995 | Murahashi et al. | 568/360 |
| 5,767,320 A | * | 6/1998 | Raja et al. | 568/360 |

FOREIGN PATENT DOCUMENTS

| | | |
|---|---|---|
| DE | 552 886 | 4/1934 |
| DE | 11 11 177 | 7/1961 |
| DE | 1 518 661 | 7/1969 |
| DE | 16 18 077 | 10/1970 |
| DE | 16 43 825 | 8/1972 |
| DE | 22 23 327 | 11/1972 |
| FR | 1.577.815 | 8/1969 |
| GB | 1147693 | 4/1969 |
| GB | 1 228 907 | 4/1971 |
| GB | 1 428 964 | 3/1976 |
| GB | 1035624 | 7/1996 |
| NL | 6 505 838 | 11/1966 |

OTHER PUBLICATIONS

Balkus, Jr., et al., J. Am. Chem. Soc. 1995, 117, 10753–10754.*

Von Franz Boich et al, "Die Luftoxydation von cyclischen Kohlenwaserstoffen in Gegenwart von Borsäure Ein beitrag zur Aufklärung des Reaktionsmechanismus", *Erdöl Und Kohle–Erdgas–Petrochemie*, May 1965, Nr. 5, pp. 360–364.

Von Horst Grasemann, "Untersuchungen über die Wirkungsweise aromatischer Kohlenwasserstoffe bei Oxydation von Cyclododecan in Gegenwart und Abwesenheit von Borsäure", *Erdöl Und Kohle–Erdgas–Petrochemie*, Dec. 1969, Nr. 12, pp. 751–754.

* cited by examiner

*Primary Examiner*—Samuel Barts
*Assistant Examiner*—Elvis O. Price
(74) *Attorney, Agent, or Firm*—Oblon, Spivak, McClelland, Maier & Neustadt, P.C.

(57) ABSTRACT

Cyclic alcohols and ketones having from 7–16 carbon atoms are prepared by a process comprising oxidizing cycloalkanes having 7–16 carbon atom s in the presence of an oxygen-containing gas and a sparingly water-soluble and sparingly aliphatic or cycloaliphatic hydrocarbon-soluble transition metal catalyst of Group 6 to Group 12 combined with a boron compound, and separating the sparingly soluble transition metal catalyst by mechanical separation after completion of the reaction.

18 Claims, No Drawings

PROCESS FOR PREPARING CYCLIC ALCOHOLS AND KETONES

BACKGROUND OF THE INVENTION

1. Field of the Invention

The present invention relates to a process for preparing cyclic alcohols and ketones having from 7–16 carbons by oxidizing cycloalkanes having from 7–16 carbons with oxygen-containing gases in the presence of sparingly water-soluble and sparingly aliphatic or cycloaliphatic hydrocarbon-soluble transition metal catalysts and boron compounds, in particular acids, oxides or esters of boron.

2. Discussion of Background

Compared to the oxidation of cyclohexane with oxygen-containing gases, larger alicyclic hydrocarbons react only slowly to give the corresponding alcohols (OL) and ketones (ON). To accelerate the reaction of cycloalkanes having from 7–16 carbon atoms, boric acid and boric acid derivatives and/or transition metal catalysts can be used in the form of their soluble salts.

Compared with the uncatalyzed reaction, boric acid causes an increase in the reaction rate and conversion rate as described in DRP 552 886, DE 16 43 825 and in the publications by H. Grasemann et at. in Erdöl, Kohle, Erdgas und Petrochemie 18 (1965), 360 and 22 (1969), 751. The boric acid causes the proportion of ketone in the product mixture to be reduced to a ratio which is typically 1:8 or less (NL 6 505 838).

In order to increase the proportion of ketone in the product mixture, transition metal catalysts can be used. U.S. Pat. No. 4,341,907 describes the use of cobalt 2-ethylhexanoate as catalyst at reaction temperatures of from 130–180° C. at a cobalt concentration of at least 1000 ppm. The reaction is conducted in the presence of pyridine. This requires an additional separation stage during workup. Pyridine has a characteristic unpleasant odor. In addition, there are a plurality of literature citations stating that pyridine is suspected of being carcinogenic.

According to DE 11 11 177, at 142° C. a conversion rate of approximately 10% and an ON/OL ratio of approximately 1:1 at a selectivity of approximately 50% are achieved. Because of the low selectivity, in addition to the desired ON/OL mixture which results from overoxidation, large amounts of an oily residue are produced which must be discarded or worked-up. The work-up requires a considerable expenditure and only partially leads to dodecanedioic acid as a utilizable product.

DE 22 23 327 describes the use of cobalt naphthenate as catalyst for oxidizing cyclohexane. At 160° C., a conversion rate of 6.5% may be achieved in this manner. However, the oxidation of cyclododecane in the absence of cobalt salts is described, using for this boric acid or similar boron compounds as the catalyst.

DE 16 18 077 claims the oxidation of cycloalkanes in the presence of a usual oxidation catalyst and in the presence of from 0.05–3% of alkyl-substituted aromatic hydrocarbons. Specific catalysts include cobalt naphthenate and other soluble cobalt salts. All of the examples of the patent solely are concerned with the oxidation of cyclohexane, the ON/OL mixture being produced at a selectivity of 76–80% and a cyclohexane conversion rate of about 3.5%.

According to GB 14 28 964, a cobalt oxime derivative is used as catalyst for the oxidation of cyclododecane at 165° C. and atmospheric pressure. 8.5% of an ON/OL mixture, based on cyclododecane used, is obtained in this manner.

The combination of boric acid and Co/Mn salts as a catalyst is mentioned in Example 5 in U.S. Pat. No. 3,419,615. At a temperature less than 155° C., virtually no reaction takes place.

Only at temperatures of from 160–170° C. is a conversion rate of about 25% achieved in a batchwise reaction procedure and about 15% in a continuous reaction procedure. Above 170° C., unwanted decomposition reactions take place. In this process, from 0.1–10 mol. % of heavy metal salt, based on the total amount, is used as the catalyst.

In the workup of the reaction mixture, the organic phase is usually washed with water or alkali metal hydroxide solutions. The above-mentioned processes use highly water-soluble heavy metal compounds which are transferred to the aqueous phase during work-up. As a result, the process is encumbered with the complex recovery of the heavy metals from the aqueous phase. In addition, the high heavy metal loading in the waste water further restricts industrial usage of these processes.

U.S. Pat. No. 5,767,320 describes the oxidation of cyclohexane in the presence of phthalocyanine complexes of various heavy metals as sole catalyst.

SUMMARY OF THE INVENTION

Accordingly, one object of the present invention is to provide a method of catalyzing the oxidation of cycloalkanes to cyclic alcohols and ketones at improved yield and selectivity and particularly improved proportionate amounts of cyclic ketone in the product.

Briefly, this object and other objects of the present invention as hereinafter will become more readily apparent can be attained by a process for preparing cyclic alcohols and ketones having from 7–16 carbons, which comprises oxidizing cycloalkanes having from 7–16 carbon atoms in the presence of an oxygen-containing gas and a sparingly water-soluble and sparingly aliphatic or cycloaliphatic hydrocarbon-soluble transition metal catalyst of Group 6 to Group 12 combined with a boron compound, and separating the sparingly soluble transition metal catalyst by mechanical separation after completion of the reaction.

DETAILED DESCRIPTION OF THE PREFERRED EMBODIMENTS

It has now been found that when a sparingly water-soluble and aliphatic or cycloaliphatic hydrocarbon-soluble transition metal catalyst (sparingly soluble complex, complex salt or a salt of a transition metal), in a particular phthalocyanine complex or a substituted phthalocyanine complex of a metal of Group 6 to Group 12 is combined with a boron compound, in particular an acid, oxide or ester of boron, substantial process improvements can be achieved in the oxidation of higher cycloalkanes.

In the process of the invention the starting cycloalkane has a carbon atom content of 7–16, in particular from 8–12, thereby producing the corresponding cyclic alcohol and ketones.

The improvements provided by the present process, in particular, are:

lower reaction temperatures, in particular temperatures below 150°;

improved conversion rates;

increased proportion of cyclic ketones in the mixture; and easier work-up of the reaction mixture.

The transition metal catalyst, i.e., a transition metal complex, a transition metal complex salt or a transition metal salt, employed in the present process is sparingly soluble or very sparingly soluble in the organic phase used as solvent, and in particular in the aqueous phase used to work-up the reaction mixture.

The low solubility of the transition metal catalyst of the invention means that the catalyst exists in the reaction mixture virtually completely as a heterogeneous suspension of finely divided solid. With good conversion rates, this produces, as a result, in particular, significant advantages in the work-up and removal of the transition metal, since the metal can be readily separated by mechanical separation processes such as filtration, sedimentation and centrifugation. Because of the very low water solubility of the transition metal complex, transition metal complex salts or transition metal salts of the invention, during the work-up of the reaction mixture, the catalyst only passes in trace amounts into the aqueous phase. The metal loading in the waste water can thus be considerably reduced in comparison to the prior art.

The catalyst isolated from the reaction mixture can be dried and then reused in the synthesis.

Suitable transition metals from which the complexes of the invention as complex salts or salts, in particular, include iron, cobalt, chromium, copper and manganese, and their mixtures. Preferably, cobalt or manganese is employed as the transition metal for the catalyst.

Suitable complexes, in particular, include phthalocyanine and substituted phthalocyanine complexes. The substituted phthalocyanine complexes are usually substituted by from 1–16 substituents which are normally in the 1, 2, 3, 4, 8, 9, 10, 11, 15, 16, 17, 18, 22, 23, 24 and 25 positions of the phthalocyanine skeleton. Preferred substituents include electron-withdrawing groups, and various substituents may be present in the molecule. Non-limiting examples of electron-withdrawing groups include halogen, nitro and cyano groups.

The metal concentration of the transition metal catalyst ranges from 0.0005–5% by weight, preferably from 0.003–1% by weight, based on the total mixture.

Suitable boron compounds include, in particular, the boron acids such as orthoboric acid and metaboric acid, boron oxide and esters of boron such as trimethyl or triethyl borate. Preferably, orthoboric and metaboric acids are used.

The concentration of the boron compound, in particular, boric acid, ranges from 0.1–25% by weight, in particular from 0.1–10% by weight, based on the total mixture.

Preferred solvents include apolar aprotic solvents such as alkanes and cycloalkanes. A particularly advantageous feature of the invention is that the cyclic alkane starting may be used as the solvent.

The oxidation reaction is conducted in the temperature range from 90–160° C., in particular from 130–150° C., and particularly preferably at from 140–150° C.

The reaction is usually conducted at atmospheric pressure. However, a superatmospheric pressure up to about 10 bar, preferably up to 5 bar, can be employed.

The reaction can be conducted batchwise or continuously.

Normally, the oxidative gas employed, in the simplest case, is dried air. However, it is also possible to employ an atmosphere containing a desired oxygen concentration in the inlet gas or exhaust gas in a specific manner by introducing nitrogen, air and/or oxygen into the reactor.

Having now generally described the invention, a further understanding can be obtained by reference to certain specific examples which are provided herein for purpose of illustration only and are not intended to be limiting unless otherwise specified.

Examples which relate to the oxidation experiments.

GENERAL

All experiments were conducted in a stainless V4A steel 5 l autoclave. Nitrogen and oxygen were introduced directly into the liquid phase above the agitator. All reactions were conducted isothermally. In the experiments the reaction temperature was controlled by an external heater via the reactor wall and an internal cooling circuit in order to remove the heat of reaction. In addition, a cooling circuit was employed to rapidly cool the products after completion of the reaction. The exhaust gas exited the reactor through a two-stage metal cooler and was freed from entrained products in a downstream gas scrubber.

COMPARATIVE EXAMPLE C1

The reactor was filled with 3.670 kg of liquid CDAN (cyclododecane) and 45 g of orthoboric acid. The mixture was heated under a blanket of nitrogen gas. At a temperature of 145° C., oxygen was added in such an amount that the oxygen content in the exhaust gas did not exceed a value of 8% by volume. After initiation of the reaction, an amount of 120 g of orthoboric acid was added to the reactor via a solids silo. Over the course of 2.5 hours, this procedure was repeated twice, each time with 65 g of boric acid. After a reaction time of 5.0 hours, the mixture was cooled and the reactor discharge hydrolyzed with water. The organic phase was separated from the aqueous boric acid and analyzed by gas chromatography. A CDAN conversion rate of 13% and yields for CDOL and CDON of 10.3% and 0.7%, respectively, were measured. This corresponds to an overall selectivity of 84.6% at an OL/ON ratio of 14.5.

COMPARATIVE EXAMPLE C2

A 3.62 kg amount of CDAN and 50 g of orthoboric acid with an additional 32 g of cobalt acetate tetrahydrate was reacted at 145° C. in the manner described in Example 1 with an oxygen-containing gas and a further 250 g of orthoboric acid. After a reaction time of 4.3 hours, a CDAN conversion rate of 22.5% and yields of 16.0% of CDOL and 2.3% of CDON at an OL/ON ratio of 6.9 were measured. This is equivalent to an overall selectivity of 81.7%.

COMPARATIVE EXAMPLE C3

In a similar manner to Comparative Example C2, 3.76 kg of CDAN, 48 g of orthoboric acid and 46 g of cobalt naphthenate were reacted at 145° C. under an oxygen-containing gas and a further 250 g of orthoboric acid. After a reaction time of 5.1 hours, a CDAN conversion rate of 21.0% and yields of 15.8% of CDOL and 2.0% of CDON at an OL/ON ratio of 7.8 were measured. This is equivalent to an overall selectivity of 84.5%.

EXAMPLE 1

In a similar manner to Comparative Example C2, 3.642 kg of CDAN, 47 g of orthoboric acid and 5.0 g of cobalt phthalocyanine were reacted at 145° C. under an oxygen-containing gas and a further 250 g of orthoboric acid. After a reaction time of 4.5 hours, a CDAN conversion rate of 19.6% and yields of 13.0% of CDOL and 3.6% of CDON at an OL/ON ratio of 3.6 were measured. This is equivalent to an overall selectivity of 84.7%.

EXAMPLE 2

In a similar manner to Comparative Example C2, 3.475 kg of CDAN, 47 g of orthoboric acid and 12.2 g of copper phthalocyanine were reacted at 145° C. under an oxygen-containing gas and a further 250 g of orthoboric acid. After a reaction time of 4.9 hours, a CDAN conversion rate of 20.6% and yields of 14.4% of CDOL and 3.2% of CDON at an OL/ON ratio of 4.5 were measured. This is equivalent to an overall selectivity of 85.4%.

EXAMPLE 3

In a similar manner to Comparative Example C2, 3.637 kg of CDAN, 48 g of orthoboric acid and 6.0 g of copper phthalocyanine were reacted at 145° C. under an oxygen-containing gas and a further 250 g of orthoboric acid. After a reaction time of 5.8 hours, a CDAN conversion rate of 22.1% and yields of 15.8% of CDOL and 3.1% of CDON at an OL/ON ratio of 5.0 were measured. This is equivalent to an overall selectivity of 85.5%.

EXAMPLE 4

In a similar manner to Comparative Example C2, 3.538 kg of CDAN, 48 g of orthoboric acid and 12.2 g of manganese phthalocyanine were reacted at 145° C. under an oxygen-containing gas and a further 250 g of orthoboric acid. After a reaction time of 4.8 hours, a CDAN conversion rate of 18.6% and yields of 13.4% of CDOL and 2.5% of CDON at an OL/ON ratio of 5.3 were measured. This is equivalent to an overall selectivity of 85.5%.

EXAMPLE 5

In a similar manner to Comparative Example C2, 3.506 kg of CDAN, 50 g of orthoboric acid and 2.0 g of cobalt hexadecafluorophthalocyanine were reacted at 145° C. under an oxygencontaining gas and a further 250 g of orthoboric acid. After a reaction time of 6.1 hours, a CDAN conversion rate of 28.8% and yields of 20.4% of CDOL and 3.2% of CDON at an OL/ON ratio of 6.4 were measured. This is equivalent to an overall selectivity of 82.3%.

EXAMPLE 6

In a similar manner to Comparative Example C2, 3.402 kg of CDAN, 47 g of orthobonc acid and 3 g of copper hexadecafluorophthalocyanine were reacted at 145° C. under an oxygencontaining gas and a further 250 g of orthoboric acid. After a reaction time of 5.6 hours, a CDAN conversion rate of 25.0% and yields of 18.0% of CDOL and 2.6% of COON at an OL/ON ratio of 6.9 were measured. This is equivalent to an overall selectivity of 82.4%.

The results of the oxidation experiments are summarized in the table below. The data show particularly marked improvement of the conversion rate and the CDON proportion in the product mixture resulting from the use of cobalt phthalocyanine.

| Example | Catalyst | Metal Content (ppm) | Conversion rate (%) | Selectivity | OL/ON | Reaction Time (h) |
| --- | --- | --- | --- | --- | --- | --- |
| C1 | — | — | 13.0 | 84.6 | 14.5 | 5 |
| C2 | Co(AcO)$_2$ | 1850 | 22.5 | 81.7 | 6.9 | 4.3 |
| C3 | Co naphthenate | 910 | 21.0 | 84.5 | 7.8 | 5.1 |
| 1 | Co phthalocyanine | 130 | 19.6 | 84.7 | 3.6 | 4.5 |
| 2 | Cu phthalocyanine | 319 | 20.6 | 85.4 | 4.5 | 4.9 |
| 3 | Cu phthalocyanine | 157 | 22.1 | 85.5 | 5.0 | 5.8 |
| 4 | Mn phthalocyanine | 115 | 18.6 | 85.5 | 5.3 | 4.8 |
| 5 | CoF$_{16}$ phthalocyanine | 31 | 28.8 | 82.3 | 6.4 | 6.1 |
| 6 | CuF$_{16}$ phthalocyanine | 49 | 25.0 | 82.4 | 6.9 | 5.6 |

(The purity data on metal contents of the phthalocyanine complexes are reported by the manufacturers of the complexes.)

Examples on the workup of the reaction mixtures:

COMPARATIVE EXAMPLE

The oxidized material of Comparative Example 2 is hydrolyzed by adding water to the reaction mixture at 90° C. The organic phase is removed by separation in a separating funnel. In the organic phase, only 16 ppm of cobalt could be detected. The cobalt acetate is more than 98% dissolved in the aqueous boric acid solution and were worked-up together with the boric acid. In this case considerable amounts of a cobalt-polluted waste water are produced.

EXAMPLE 7

The oxidized material of Example 1 is hydrolyzed by adding water at 90° C. The organic phase is separated in a separating funnel. The water-insoluble cobalt phthalocyanine is separated by filtration and dried under reduced pressure at 60–80° C. In this manner the catalyst was virtually quantitatively recovered and reused in the reaction. The cobalt-free aqueous boric acid solution were then worked-up, e.g. by crystallization.

The disclosure of German priority Application Number 19903152.5 filed Jan. 27, 1999 is hereby incorporated by reference into the present application.

Obviously, numerous modifications and variations of the present invention are possible in light of the above teachings. It is, therefore, to be understood that within the scope of the appended claims, the invention may be practiced otherwise than as specifically described herein.

What is claimed as new and is intended to be secured by letters patent is:

1. A process for preparing cyclic alcohols and ketones having from 7–16 carbons, which comprises:
   oxidizing cycloalkanes having from 7–16 carbon atoms in the presence of an oxygen-containing gas and a sparingly water-soluble and sparingly aliphatic or cycloaliphatic hydrocarbon-soluble transition metal catalyst of Group 6 to Group 12 combined with a boron compound; and
   separating the sparingly soluble transition metal catalyst by mechanical separation after completion of the reaction.

2. The process as claimed in claim 1, wherein the transition metal of said transition metal catalyst is iron, cobalt, chromium, copper or manganese.

3. The process as claimed in claim 1, wherein the transition metal catalyst is a phthalocyanine complex.

4. The process as claimed in claim 1, wherein the transition metal catalyst is a substituted phthalocyanine complex.

5. The process as claimed in claim 4, wherein the substituted phthalocyanine has at least one electron-withdrawing substituent.

6. The process as claimed in claim 5, wherein the electron-withdrawing substituent is a halogen, nitro, cyano group or combination thereof.

7. The process as claimed in claim 1, wherein the concentration of the metal of the transition metal catalyst ranges from 0.0005–5% by weight.

8. The process as claimed in claim 7, wherein the concentration of the metal of the transition metal catalyst ranges from 0.003–1% by weight.

9. The process as claimed in claim 1, wherein said boron compound is orthoboric or metaboric acid.

10. The process as claimed in claim 1, wherein the concentration of the boron compound ranges from 0.1–25% by weight.

11. The process as claimed in claim 10, wherein the concentration of the boron compound ranges from 0.1–10% by weight.

12. The process as claimed in claim 1, wherein the cycloalkane has from 8–12 carbons.

13. The process as claimed in claim 1, wherein the reaction temperature ranges from 90–160° C.

14. The process as claimed in claim 13, wherein the reaction temperature ranges from 130–150° C.

15. The process as claimed in claim 1, wherein the reaction is conducted in an aprotic solvent.

16. The process as claimed in claim 15, wherein the aprotic solvent is an alkane or a cycloalkane.

17. The process as claimed in claim 16, wherein the cycloalkane solvent is the cycloalkane reactant.

18. The process as claimed in claim 3, wherein after the oxidizing the cycloalkanes form a mixture of cyclic alcohols and cyclic ketones; and a ratio of the cyclic alcohols to the cyclic ketones in the mixture is 6.9 or less.

* * * * *